United States Patent [19]

Lin et al.

[11] Patent Number: 4,982,024

[45] Date of Patent: Jan. 1, 1991

[54] PROCESS FOR THE SELECTIVE DEHYDROHALOGENATION OF AN ADMIXTURE OF ALKYLHALIDES

[75] Inventors: Kaung-Far Lin, Baton Rouge; Joseph A. Bossier, Greenwell Springs, both of La.; George H. Ransford, Magnolia, Ak.

[73] Assignee: Ethyl Corporation, Richmond, Va.

[21] Appl. No.: 456,969

[22] Filed: Dec. 26, 1989

[51] Int. Cl.$^5$ .............................................. C07C 17/38
[52] U.S. Cl. ................................... 570/262; 585/641; 423/481; 423/488; 203/DIG. 6
[58] Field of Search ...................... 570/262; 585/641; 203/DIG. 6; 423/481, 488

[56] References Cited

U.S. PATENT DOCUMENTS 4,024,189  5/1977  Davis ............................... 260/585 A

*Primary Examiner*—Howard T. Mars
*Attorney, Agent, or Firm*—E. E. Spielman, Jr.

[57] ABSTRACT

A process for the dehydrohalogenation of a feed comprised of an admixture of primary, secondary and tertiary alkylhalides to selectively convert the secondary and tertiary alkylhalides of the admixture to olefins by dehydrohalogenation, with minimal conversion, if any, of the primary alkylhalides. The reaction, which is particularly applicable to the selective dehydrobromination of an admixture of primary, secondary and tertiary alkylbromides, is carried out in a distillation-reaction zone, column, or distillation-reactor, to simultaneously (i) convert the secondary and tertiary alkylbromides to olefins and hydrogen bromide, and (ii) separate the olefins and hydrogen bromide, (iii) and the primary alkyl bromides, from the reaction mixture.

18 Claims, 1 Drawing Sheet

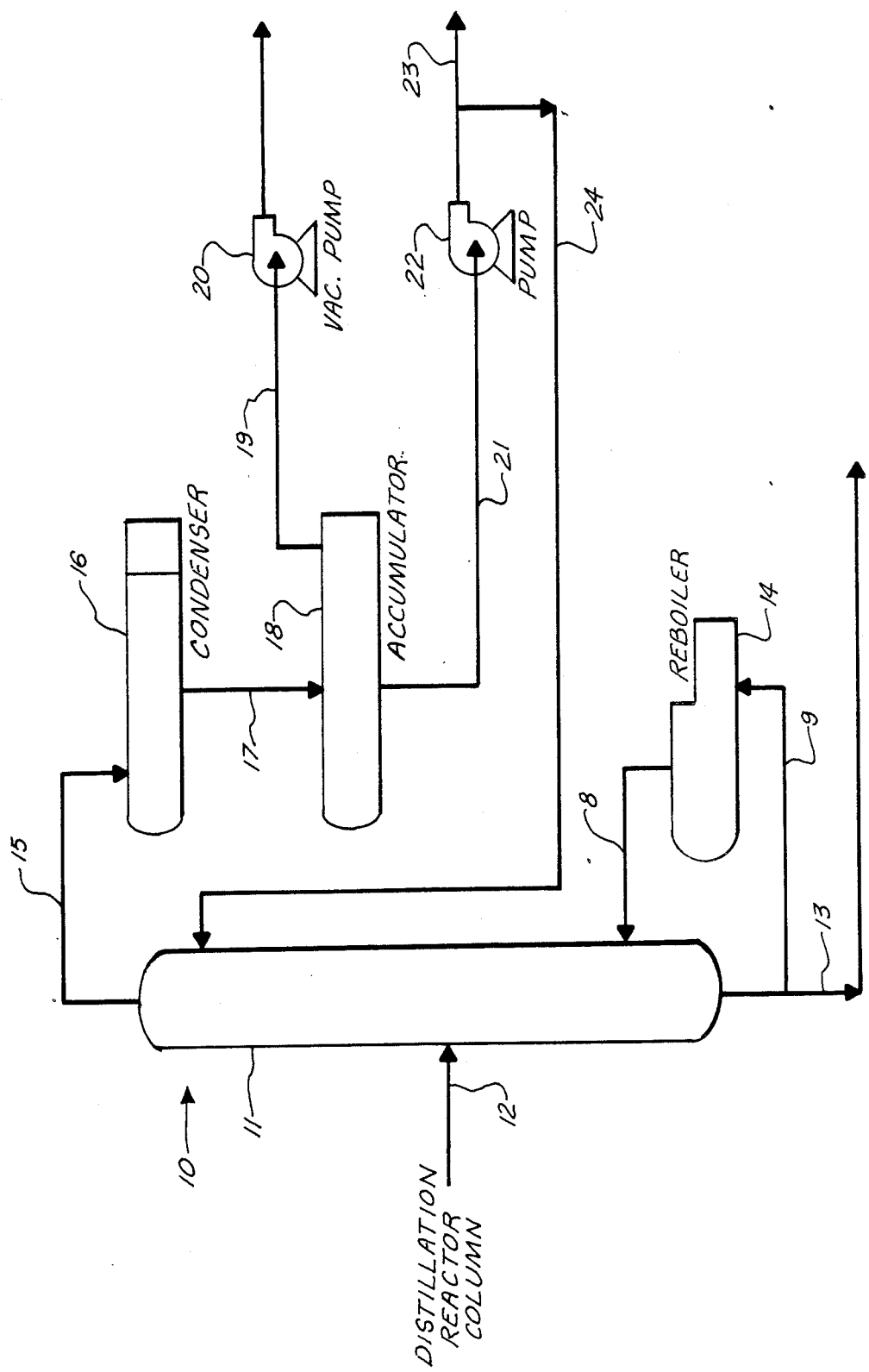

PROCESS FOR THE SELECTIVE DEHYDROHALOGENATION OF AN ADMIXTURE OF ALKYLHALIDES

FIELD OF THE INVENTION

A process for the selective dehydrohalogenation of a feed comprised of an admixture of primary, secondary and tertiary alkylhalides. In particular, it relates to a process for the selective dehydrobromination of a feed comprised of an admixture of primary, secondary and tertiary alkylbromides for conversion of the secondary and tertiary alkylbromides to olefins, with minimal conversion, if any, of the primary alkylbromides, and simultaneous separation of primary alkylbromides from the reaction mixture.

BACKGROUND

It is known to hydrohalogenate a feed rich in straight chain terminal olefins, or alpha olefins, to produce hydrohalogenated alkanes comprised predominantly of straight chain alkyl groups particularly useful in the production of linear tertiary amines, or alkyl dimethyl amines. As a class the linear tertiary amines are useful as surface active agents, e.g., surfactants, soaps, cleansing and other personal care products.

It is also known to produce linear tertiary amines, or alkyl dimethyl amines, starting with a mixed olefin feed, viz., vinyl olefins and internal olefins, or vinyl olefins and vinylidene olefins, or admixture of vinyl olefins, internal olefins and vinylidene olefins. U.S. Pat. No. 4,024,189, which was issued on May 17, 1977 to Wayne T. Davis, describes a process of this type. In a first step, where vinylidene olefins are present in appreciable quantities, the feed is generally selectively isomerized to convert the vinylidene olefins to branched chain internal olefins. The admixture of vinyl olefins and internal olefins is, in either event, next hydrohalogenated. Suitably, the admixture of olefins is hydrohalogenated at conditions which promote the AntiMarkovnikoff addition of the hydrogen halide to the olefin. In the production of linear tertiary amines from a mixed olefin feed, it is essential after the hydrohalogenation step to separate the 1-haloalkanes from the secondary and tertiary haloalkanes, and thereby concentrate the 1-haloalkanes prior to amination of the 1-haloalkanes to form aminehydrohalides. The aminehydrohalides are then neutralized to convert them to linear tertiary amines.

The 1-haloalkanes are concentrated in a stream for subsequent amination, and neutralization, by selective dehydrohalogenation. Thus, the feed constituted of an admixture of primary, secondary and tertiary haloalkanes, or bromoalkanes, is next selectively dehydrohalogenated, or dehydrobrominated. In the reaction, the hydrogen halide, or hydrogen bromide, is removed from the reaction mixture by sparging with nitrogen. The mixture of olefins and alkylhalides, or alkylbromides, is then subjected to a separate distillation to remove the olefins, and the alkylhalides, or alkylbromides, and then recovered.

A straight chain olefin, particularly an alpha olefin, is the raw material of choice in conducting this process because the surface active properties of a straight chain derivative thereof is superior for a given molecular weight vis-a-vis their branched chain isomers. Substitution in the 1-position of the alpha olefin yields more stable and effective products. For this reason, in the production of alkyl dimethyl amines it is sometimes current practice to use a blended olefin feed constituted essentially of alpha olefins as the raw feed. Because of the relatively high cost of high purity alpha olefin feeds vis-a-vis the lower cost and greater availability of mixed olefin feeds however, there exists a clear present need for processes which can economically handle mixed olefin feeds.

OBJECTS

It is, accordingly, a primary objective of this invention to fulfill this need, and others.

In particular, it is an object to provide a process for upgrading the primary linear alpha halide content in an alkylhalide stream which contains primary, secondary and tertiary alkylhalides, as produced, e.g., by the hydrohalogenation of a mixed olefin feed.

A specific object is to provide a process for dehydrobrominating an alkylbromide stream which contains primary, secondary and tertiary alkylbromides to selectively convert secondary and tertiary alkylbromides to olefins, and hydrogen bromide, without significant dehydrobromination of the primary alkylbromides components of the feed.

A yet further and more specific object is to provide a process for simultaneously dehydrobrominating an alkylbromide stream constituted of primary, secondary and tertiary alkylbromides, as produced in an upstream olefin-hydrobromination reactor, to simultaneously convert the secondary and tertiary alkylbromides to olefins and hydrogen bromide, while separating the olefins and hydrogen bromide from the reacting mixture, and recovering the Primary alkylbromide. The primary alkylbromide product is suitable for downstream amination to primary aminehydrobromides; the latter of which is suitable for subsequent neutralization to linear tertiary amines.

THE INVENTION

These objects and others are accomplished in accordance with this invention embodying, generally, a process for dehydrohalogenating a feed admixture constituted of primary, secondary and tertiary alkylhalides in a distillation-reaction zone, distillation reactor column, or vessel, to simultaneously (i) convert the secondary and tertiary alkylhalides to olefins and hydrogen halide, (ii) separate off the olefins and hydrogen bromide, and (iii) concentrate the primary alkylhalides for recovery. The liquid alkylhalide feed stream, pursuant to the invention, is introduced into the distillation-reactor column, preferably above the center of the column, at temperature and residence time sufficient to dehydrohalogenate and convert the secondary and tertiary alkylhalides, branched chain or straight chain, or both, to olefins and gaseous hydrogen halide. Vaporized components of the feed, and gaseous hydrogen halide, ascend or rise within the column, which may be packed, or preferably provided with sieve, valve, or bubble trays, or the functional equivalents thereof, while a boiling liquid is collected at the bottom of the column, where heat is applied as via a reboiler or still. The bottom product is constituted of a liquid rich in primary alkylhalides, whereas olefins as condensate and hydrogen halide gas are removed from the overhead, or top of the column, and a portion of the olefins returned to the column as reflux.

The secondary and tertiary alkylhalides of the feed are converted to olefins and hydrogen halide in the dehydrohalogenation reaction, the vaporous olefin and gaseous hydrogen halide ascending within the column. The less volatile, or higher boiling components, notably the primary alkylhalide, is concentrated within the lower portion of the column. To increase the concentration of the lower boiling components within the ascending vapor and to remove the higher boiling component, or components, the overhead olefin product is condensed, a portion thereof is recovered, and a portion of the liquid olefin as recycle liquid, generally at, or near, its boiling point, is recycled and brought into intimate countercurrent contact with the ascending stream of vapor. The hydrogen halide is separately recovered as a product. At all levels within the column, some low boiling components diffuse from the liquid into the vapor, vaporizing as the components are passed from one phase into another. The heat of vaporization of the low boiling components is supplied by an equal amount of heat of condensation of the high boiling components. High boiling components diffuse spontaneously from vapor to liquid. The net effect is that high boiling components are transferred from vapor to liquid, and a thermally equivalent amount of the low boiling components are transferred from liquid to vapor. As the vapor rises in the column, it becomes enriched in the low boiling components. As the liquid descends through the column, its content of high boiling components is increased. The bulk flow of low boiling components is therefore up the column, while the higher boiling components flow down the column.

In its operation and function, the distillation-reactor is dual functional. It is a vessel or enclosure wherein the secondary and tertiary alkylhalides components of the feed are dehydrohalogenated to form olefins and hydrogen halide. However, it also functions as a distillation column to separate out any unreacted feed components, particularly the primary alkylhalides, from the reaction products, notably the olefins and hydrogen halide formed from the secondary and tertiary alkylhalides in the dehydrohalogenation reaction. In its overall operation and function however, it differs profoundly from prior art procedures for the dehydrohalogenation of an admixture of primary, secondary and tertiary alkylhalides in a first step, or plurality of steps, followed by separate distillation to separate and recover primary alkylhalides from the reaction product mixture. A basic difference is that the dehydrobromination reaction itself occurs primarily in a liquid phase from which the reaction products, viz., olefins and halogen halide, are rapidly and continuously evolved into the vapor phase. Consequently, a normally reversible reaction is driven virtually to completion, minimizing competing reactions and improving the efficiency and effectiveness of the process. The olefins can be recovered as high purity coproducts, reactor time reduced, and there is minimal loss, if any, of primary linear alkylhalides. The selective dehydrohalogenation reaction and distillation are carried out continuously in a single piece of equipment.

The process of this invention is particularly applicable to the selective dehydrobromination of an admixture of primary, secondary and tertiary alkylbromides; whether the alkylbromides are branched chain or linear, or both. In a distillation-reaction zone, column, or distillation-reactor such as described, an alkylbromide feed stream of this composition readily simultaneously (i) converts the secondary and tertiary alkylbromide to olefins and hydrogen bromide, (ii) separates the olefins and hydrogen bromide from the reacting mixture, these components being evolved from the top of the column, and (iii) separates the primary alkylbromide from the reacting mixture, this component being removed from the bottom of the column.

REFERENCE TO THE FIGURE

A distillation-reactor column suitable for the practice of this invention is described by reference to the FIGURE. The FIGURE schematically depicts a side elevation view of a preferred distillation-reactor, as used in carrying out the selective dehydrobromination of a feed constituted of an admixture of primary, secondary and tertiary alkylhalides, with the simultaneous separation of olefin and hydrogen halide coproducts from the top of the distillation-reactor, and separation of primary alkylhalide from the bottom of the distillation reactor. The principle of operation of the distillation-reactor will be understood by reference to the following detailed description which makes direct reference to the FIGURE in describing a typical operation.

The distillation-reactor 10, reference being made first generally to the FIGURE, is constituted of a column formed by an enclosing wall 11, provided with a feed inlet 12, bottom liquid product outlet 13, a reboiler 14, or still, and overhead vapor outlet 15 for removal of coproducts. The vaporous coproducts removed from the top of distillation-reactor 10 are heat exchanged and at least partially liquified within a condenser 16 at the top of the column. The coproducts from the condenser 16 are passed via line 17 to an accumulator 18. A gaseous halogen halide product is removed via a gas outlet from the top of the accumulator 18, with the aid of a vacuum pump 20, and pumped via line 19 to a recovery vessel; or recycled. A liquid olefin coproduct is removed via an outlet at the bottom of the accumulator 18, and pumped through line 21 via the use of a pump 22. A first portion of the liquid olefin coproduct is passed via line 23 to a storage vessel for recovery, while a second portion of the liquid olefin product is recycled to the top of the column 11 via line 24 as reflux. The inside of the column can be provided with trays, plates or packings as typically used in distillation towers. In carrying out the process of this invention, typically from about 5 to about 50, preferably from about 10 to about 20 trays or plates (actual or theoretical), are employed dependent to some extent on the amount of olefin and hydrogen halide coproduct that is to be separated, and the molecular weights of the alkylhalides contained within the feed. The feed is generally introduced above the middle and near the top of the column, generally at about the level where the temperature would boil off and drive a large amount of the lighter boiling components up the column, and permit a major amount of the higher boiling components to descend to the bottom of the column. The dehydrohalogenation takes place primarily in the bottom portion of the distillation reactor, while the mid portion and upper portion of the distillation-reactor constitutes largely stripping and rectifying sections for minimizing the carryover of alkylhalides in the overhead olefin stream.

The design of the column may optionally be different above and below the feed point. For example, it may be chosen to have a section below the feed point consisting of trays and a section above the feed point consisting of packings. The section above the feed point can have a smaller diameter than the diameter of the section below the feed point.

The feed, prior to introduction via line 12 into the column, may be preheated, if desired. The reboiler 14, on the other hand, receives liquid from the bottom of the column via line 9, and returns the heated liquid to the column via line 8. The bottoms product is removed from the column via line 13.

The temperature and residence time of the liquid within the column are two of the more important of the major operating variables. The temperature of the column, and reaction, is controlled by setting the temperature at the bottom of the column, and by system pressure. The bottom temperature controls the temperature gradient established throughout the column, or temperature at the different levels of the column, and the operating pressure. Preferably the bottom temperature, or temperature of operation of the reboiler 14, dependent on the composition of the feed, ranges from about 400° F. to about 700° F., more preferably from about 500° F. to about 580° F. The bottom temperature in any given operation must, of course, be sufficiently high to maintain the temperature of the olefin stream removed from the top of the column above its dew point, at the pressure existing in the column. The bottom temperature, on the other hand, should not be high enough to produce cracking, or pyrolysis. The column pressure generally ranges from about 1 pound per square inch absolute, psia, to about 45 psia, more generally from about 5 psia to about 20 psia. The residence time must be sufficient to permit essentially complete dehydrohalogenation of the secondary and tertiary olefins, and hence is dependent on feed composition. Generally, a residence time of the liquid within the column ranges from about 10 minutes to about 2 hours, more often from about 20 minutes to about 30 minutes, to complete the dehydrohalogenation of the secondary and tertiary alkylhalides.

The distillation-reaction is carried out such that the rising vapor is contacted with a condensed portion of previously evolved vapor; a transfer of material and an exchange of heat occurring as a result of the contact. Vapor is removed from the top of the distillation-reactor, the vapor is condensed and liquid olefins returned to the top of the column as reflux to produce greater enrichment of the vapor in the olefins than possible in a single distillation using the same amount of heat. The reflux is generally set at a liquid:distillate ratio ranging from about 0.1:1 to about 10:1, or higher, preferably from about 0.2:1 to about 2:1, based on the quantity of olefins recycled to the column vis-a-vis the quantity of olefins removed as distillate from the process as a coproduct, or coproducts.

The following examples, and comparative data, are exemplary of a preferred process for the practice of this invention.

EXAMPLES

In a first dehydrobromination run, the sixth tray from the top of a distillation-reactor containing a total of fifteen trays, was charged with a feed constituting an admixture of primarily primary linear (1° linear), primary branched (1° branched), secondary and tertiary alkylbromides. The column was fed with the admixture at a rate of 6.5 lbs./hr., a two-minute liquid residence time was provided for each of the fifteen trays (a total of 30 minutes), and the bottom temperature of the distillation-reactor was maintained sufficient to provide a column pressure of 5 pounds per square inch absolute, psia. The coproducts of the distillation-reaction was removed from the column overhead at a rate of 0.6 lbs./hr. condensed, a portion of the olefins returned to the top of the column as liquid reflux, and the balance of the liquid olefin and hydrogenbromide recovered. A product, essentially primary alkylbromides, i.e., 1° alkylbromides, was removed from the bottom of the distillation-reactor at a rate of 6.1 lbs./hr.

Reference is made to the following Table 1 which gives the composition of the feed (Mole %) to the distillation-reactor unit, and the overall composition (Mole %), and temperature, of the liquid at different selected tray levels within the distillation-reactor. Additionally, the composition (Mole %) held on each of these trays, and overhead, is given on an "Olefin free basis" and on an "Alkylbromide free" basis, respectively.

TABLE 1

| Feed Comp. Mole % | | | | | |
|---|---|---|---|---|---|
| | 1° Linear | | 90.2 | | |
| | 1° Branched | | 3.5 | | |
| | Secondary | | 6.3 | | |
| | Tertiary | | 0 | | |
| | Olefins | | 0 | | |

| Component, Mole % (Temperature) | Bot Comp (517 F.) | Tray 12 (483 F.) | Tray 9 (462 F.) | Tray 4 (417 F.) | Ovhd |
|---|---|---|---|---|---|
| 1° Linear | 97.2 | 90.7 | 76.7 | 35 | 8.2 |
| 1° Branched | 1.6 | 2.5 | 2.9 | 2.2 | 0.5 |
| Secondary | 0.3 | 0.6 | 2.7 | 4.1 | 5.7 |
| Tertiary | 0 | 0 | 0 | 0 | 0 |
| Vinyl | 0 | 0.3 | 0.9 | 2.6 | 4 |
| 2 Int | 0.3 | 2.2 | 5.6 | 16.8 | 21.9 |
| 3+ Int | 0.5 | 3 | 9.4 | 32.1 | 52.4 |
| Vd | 0 | 0.6 | 1.6 | 6.6 | 7 |
| Trisub | 0 | 0.1 | 0.2 | 0.6 | 0.3 |

| (OLEFIN FREE BASIS) | | | | | |
|---|---|---|---|---|---|
| Component | Bot Comp. | Tray 12 | Tray 9 | Tray 4 | Ovhd |
| Total Percent | 99.1 | 93.8 | 82.3 | 41.3 | 14.4 |
| 1° Linear | 98.1 | 96.7 | 93.2 | 84.7 | 56.9 |
| 1° Branched | 1.6 | 2.7 | 3.5 | 5.3 | 3.5 |
| Secondary | 0.3 | 0.6 | 3.3 | 9.9 | 39.6 |
| Tertiary | 0 | 0 | 0 | 0 | 0 |

| (ALKYLBROMIDE FREE BASIS) | | | | | |
|---|---|---|---|---|---|
| Component | Bot Comp | Tray 12 | Tray 9 | Tray 4 | Ovhd |
| Total Percent | 0.8 | 6.2 | 17.7 | 58.7 | 85.6 |
| Vinyl | 0 | 4.8 | 5.1 | 4.4 | 4.7 |
| 2 Int | 37.5 | 35.5 | 31.6 | 28.6 | 25.6 |
| 3+ Int | 62.5 | 48.4 | 53.1 | 54.7 | 61.2 |
| Vd | 0 | 9.7 | 9 | 11.2 | 8.2 |
| Trisub | 0 | 1.6 | 1.1 | 1 | 0.4 |

In a second dehydrobromination run the ninth tray from the top of the distillation-reactor column was fed with a mixed feed at a rate of 5.5 lbs./hr. as identified in Table 2. Coproducts were removed from the overhead of the column at a rate of 1.46 lbs./hr. without the return of any liquid reflux. Again the column was operated at 5 psia. A bottom product was removed at a rate of 4.1 lbs./hr. Table 2 gives the feed composition (Mole %), and temperature of the liquid at selected tray levels throughout the reactor. Table 2 also gives the liquid feed composition (Mole %) of the different trays on an "Olefin free basis" and on an "Alkylbromide free basis", respectively.

TABLE 2

| 1° Linear | 78.9 |
|---|---|
| 1° Branched | 3.3 |
| Secondary | 13.1 |
| Tertiary | 4.7 |

TABLE 2-continued

| | Feed Comp. Mole % | | Olefins | | N.D. |
|---|---|---|---|---|---|
| Component, Mole % (Temperature-) | Bot Comp (516 F.) | Tray 12 (480 F.) | Tray 9 | Tray 4 (419 F.) | Ovhd (380 F.) |
| 1° Linear | 96.1 | 88.9 | 76.7 | 54.1 | 14 |
| 1° Branched | 2.6 | 2.7 | 2.2 | 3.2 | 0.9 |
| Secondary | 0.6 | 3.5 | 11.1 | 10.7 | 4.6 |
| Tertiary | 0 | N.D. | N.D. | N.D. | N.D. |
| Vinyl | N.D. | 0.3 | 0.5 | 1.3 | 3.7 |
| 2 Int | 0.7 | 1 | 2.4 | 8.6 | 21.1 |
| 3+ Int | *** | 1.8 | 1.5 | 5.6 | 17.9 |
| Vd | N.D. | 0.1 | 0.4 | 1.1 | 1 |
| Trisub | N.D. | 1.7 | 5.2 | 15.4 | 36.7 |

| Component | Bot Comp | Tray 12 | Tray 9 | Tray 4 | Ovhd |
|---|---|---|---|---|---|
| Total Percent | 99.3 | 95.1 | 90 | 68 | 19.5 |
| 1° Linear | 96.8 | 93.5 | 85.2 | 79.6 | 71.8 |
| 1° Branched | 2.6 | 2.8 | 2.4 | 4.7 | 4.6 |
| Secondary | 0.6 | 3.7 | 12.3 | 15.7 | 23.6 |
| Tertiary | 0 | 0 | 0 | 0 | 0 |
| Total Percent | 0.7 | 4.9 | 10 | 32 | 80.4 |
| Vinyl | 0 | 6.1 | 5 | 4.1 | 4.6 |
| 2 Int | 100 | 20.4 | 24 | 26.9 | 26.2 |
| 3+ Int | 0 | 36.7 | 15 | 17.5 | 22.3 |
| Vd | 0 | 2 | 4 | 3.4 | 1.2 |
| Trisub | 0 | 34.7 | 52 | 48.1 | 45.6 |

***:Internals Are Lumped Together.

A third demonstration run was made essentially as described with reference to the second demonstration run. Essentially the same feed and feed rate were employed as in the second demonstration run; the feed again entering on Tray 9 while the column was operated at 5 psia. In this instance however, 0.9 lbs./hr. of liquid reflux was returned to the overhead of this column, with the total overhead rate being 1.2 lbs./hr. Product was removed from the bottom of the distillation-reactor at a rate of 5.4 lbs./hr. The data for this operation are given in Table 3.

TABLE 3

| | | 1° Linear | 78.9 |
|---|---|---|---|
| | | 1° Branched | 3.3 |
| | | Secondary | 13.1 |
| | | Tertiary | 4.7 |
| Feed Comp. Mole % | | Olefins | N.D. |

| Component, Mole % (Temperature) | Bot Comp (516 F.) | Tray 12 (471 F.) | Tray 9 | Tray 4 (406 F.) | Ovhd (365 F.) |
|---|---|---|---|---|---|
| 1° Linear | 93 | 82.2 | 71.7 | 34.9 | 8.1 |
| 1° Branched | 2.7 | 3.1 | 2.5 | 1.8 | 0.4 |
| Secondary | 0.8 | 5 | 10.2 | 10 | 2.7 |
| Tertiary | N.D. | N.D. | N.D. | N.D. | N.D. |
| Vinyl | 0.3 | 0.6 | 0.8 | 1.4 | 3.8 |
| 2 Int | 1.9 | 1.7 | 6 | 7.7 | 17.1 |
| 3+ Int | 0.8 | 3.2 | *** | 19.1 | 20.8 |
| Vd | N.D. | 0.3 | 0.5 | 1.3 | 1.4 |
| Trisub | 0.5 | 4 | 8.2 | 23.7 | 45.8 |

(OLEFIN FREE BASIS)

| Component | Bot Comp | Tray 12 | Tray 9 | Tray 4 | Ovhd |
|---|---|---|---|---|---|
| Total Percent | 96.5 | 90.3 | 84.4 | 46.7 | 11.2 |
| 1° Linear | 96.4 | 91 | 85 | 74.7 | 72.3 |
| 1° Branched | 2.8 | 3.4 | 3 | 3.9 | 3.6 |
| Secondary | 0.8 | 5.5 | 12.1 | 21.4 | 24.1 |
| Tertiary | 0 | 0 | 0 | 0 | 0 |

(ALKYLBROMIDE FREE BASIS)

| Component | Bot Comp | Tray 12 | Tray 9 | Tray 4 | Ovhd |
|---|---|---|---|---|---|
| Total Percent | 3.5 | 9.8 | 15.5 | 53.2 | 88.9 |
| Vinyl | 8.6 | 6.1 | 5.2 | 2.6 | 4.3 |
| 2 Int | 54.3 | 17.3 | 38.7 | 14.5 | 19.2 |
| 3+ Int | 22.9 | 32.7 | 0 | 35.9 | 23.4 |
| Vd | 0 | 3.1 | 3.2 | 2.4 | 1.6 |
| Trisub | 14.3 | 40.8 | 52.9 | 44.5 | 51.5 |

In the previously described runs it will be observed that the overhead contained 14.4 mole %, 19.5 mole %, and 11.2 mole % alkylbromide, respectively. Additional trays can be added to further reduce the amount of alkylbromide. To demonstrate this, a fourth run was made by introducing the feed containing the admixture of primary linear, primary branched, secondary and tertiary alkylbromides to the 12th tray, counting from the top of the distillation reactor column; wherein the column contains a total of 15 distillation trays. Thus, a C14 feed of 13 mole % alkylbromide (1° Linear, 1° Branched, Secondary and Tertiary alkylbromides) and 87 mole % olefins was fed to tray 12 of a 15 tray distillation column at 6.5 lb./hr., and HBr was fed to the headspace of the reboiler at 0.37 lb./hr. The column pressure was controlled at 5 psia, and no reflux was added to the overhead. As will be observed from the data given in Table 4 the liquid product from the overhead contained only 1 mole % alkylbromide. Thus, with additional trays in the rectifying section the amount of alkylbromide in the overhead liquid can be greatly reduced; particularly by a combination of additional trays and reflux.

TABLE 4

| | | 1° Linear | 10.3 |
|---|---|---|---|
| | | 1° Branched | 0.4 |
| | | Secondary | 1.7 |
| | | Tertiary | 0.6 |
| | | Vinyl | 74.3 |
| | | Internal | 3.7 |
| Feed Comp. Mole % | | Vd/Tri | 8.9 |

| Component, Mole % (Temperature) | Bot Comp (436 F.) | Tray 12 (N.R.) | Tray 9 (404 F.) | Tray 4 (393 F.) | Ovhd (380 F.) |
|---|---|---|---|---|---|
| 1° Linear | 24.5 | 5 | 0.6 | 0.2 | 0.2 |
| 1° Branched | 0.8 | 0.2 | N.D. | N.D. | N.D. |
| Secondary | 3 | 1.8 | 1.2 | 1.3 | 0.8 |
| Tertiary | N.D. | N.D. | N.D. | N.D. | N.D. |
| Vinyl | 56.8 | 76 | 80.9 | 80.3 | 80.7 |
| 2 Int | 5.7 | 5.6 | 7.1 | 7.1 | 6.1 |
| 3+ Int | 0.3 | 0.5 | 0.7 | 0.6 | 1.8 |
| Vd | 1 | 2.8 | 1.2 | 0.9 | 0.7 |
| Trisub | 8 | 8.1 | 8.4 | 9.6 | 9.7 |

(OLEFIN FREE BASIS)

| Component | Bot Comp | Tray 12 | Tray 9 | Tray 4 | Ovhd |
|---|---|---|---|---|---|
| Total Percent | 28.3 | 7 | 1.8 | 1.5 | 1 |
| 1° Linear | 86.6 | 71.4 | 33.3 | 13.3 | 20 |
| 1° Branched | 2.8 | 2.9 | 0 | 0 | 0 |
| Secondary | 10.6 | 25.7 | 66.7 | 86.7 | 80 |
| Tertiary | 0 | 0 | 0 | 0 | 0 |

(ALKYLBROMIDE FREE BASIS)

| Component | Bot Comp | Tray 12 | Tray 9 | Tray 4 | Ovhd |
|---|---|---|---|---|---|
| Total Percent | 71.8 | 93 | 98.3 | 98.5 | 99 |
| Vinyl | 79.1 | 81.7 | 82.3 | 81.5 | 81.5 |
| 2 Int | 7.9 | 6 | 7.2 | 7.2 | 6.2 |
| 3+ Int | 0.4 | 0.5 | 0.7 | 0.6 | 1.8 |
| Vd | 1.4 | 3 | 1.2 | 0.9 | 0.7 |

TABLE 4-continued

| Trisub | 11.1 | 8.7 | 8.5 | 9.7 | 9.8 |

It is apparent that various modifications and changes can be made without departing the spirit and scope of this invention, as will be apparent to those skilled in this art.

Having described the invention, what is claimed is:

1. In a process for the selective dehydrohalogenation of a liquid feed comprising an admixture of primary, secondary and tertiary alkylhalides to convert the secondary and tertiary alkylhalides to olefins, with minimum dehydrohalogenation of the primary alkylhalides,
the improvement comprising
introducing said liquid alkylhalide feed stream into a staged distillation-reactor column at temperature and residence time sufficient to dehydrohalogenate and convert the secondary and tertiary alkylhalides components of said liquid feed stream to vaporous olefins and gaseous hydrogen halide, the vaporous olefins, and gaseous hydrogen halide ascending through the distillation-reactor column,
condensing and recovering vaporous olefins at the top of the column, withdrawing the hydrogen halide and one portion of the condensed olefins as coproducts, and recycling as reflux a second portion of the condensed olefins into the top of the column, the recycled liquid olefins passing downwardly through the column as a boiling stream which countercurrently intimately contacts said ascending vaporized and gaseous components throughout the length of the column, the rising vapor at or near its condensing temperature becoming enriched in olefins and gaseous hydrogen halide, with the descending liquid at or near its boiling temperature becoming enriched in primary alkylhalides, and
withdrawing primary alkylhalides from the bottom of the column.

2. The process of claim 1 wherein the distillation-reactor column is provided with from about 5 to about 50 stages.

3. The process of claim 2 wherein the distillation-reactor column is provided with from about 10 to about 20 stages.

4. The process of claim 1 wherein the temperature at the bottom of the distillation-reactor ranges from about 400° F. to about 700° F.

5. The process of claim 4 wherein the temperature at the bottom of the distillation-reactor ranges from about 500° F. to about 580° F.

6. The process of claim 1 wherein the temperature at the bottom of the distillation-reactor ranges from about 400° F. to about 700° F. and the total liquid residence time ranges from about 10 minutes to about 2 hours.

7. The process of claim 1 wherein the temperature at the bottom of the distillation-reactor ranges from about 500° F. to about 580° F., and the total liquid residence time ranges from about 20 minutes to about 30 minutes.

8. The process of claim 1 wherein condensed liquid olefins are returned to the top of the distillation-reactor column as reflux in liquid:distillate ratio ranging from about 0.1:1 to about 10:1.

9. The process of claim 1 wherein condensed liquid olefins are returned to the top of the distillation-reactor column as reflux in liquid-distillate ratio ranging from about 0.2:1 to about 2:1.

10. In a process for the selective dehydrobromination of a liquid feed comprising an admixture of primary, secondary and tertiary alkylbromides to convert the secondary and tertiary alkylbromides to olefins, with minimum dehydrobromination of the primary alkylbromides,
the improvement comprising
introducing said liquid alkylbromide feed stream into a staged distillation-reactor column at temperature and residence time sufficient to dehydrobrominate and convert the secondary and tertiary alkylbromides components of said liquid feed stream to vaporous olefins and gaseous hydrogen bromide, the vaporous olefins, and gaseous hydrogen bromide ascending through the column,
condensing and recovering vaporous olefins at the top of the column, withdrawing the hydrogen bromide and one portion of the condensed olefins as coproducts, and recycling as reflux a second portion of the condensed olefins into the top of the column, the recycled liquid olefins passing downwardly through the column as a boiling stream which countercurrently intimately contacts said ascending vaporized and gaseous components throughout the length of the column, the rising vapor at or near its condensing temperature becoming enriched in olefins and gaseous hydrogen bromide, with the descending liquid at or near its boiling temperature becoming enriched in primary alkylbromides, and
withdrawing primary alkylbromides from the bottom of the column.

11. The process of claim 10 wherein the distillation-reactor column is provided with from about 5 to about 50 stages.

12. The process of claim 11 wherein the distillation-reactor column is provided with from about 10 to about 20 stages.

13. The process of claim 10 wherein the temperature at the bottom of the distillation-reactor ranges from about 400° F. to about 700° F.

14. The process of claim 13 wherein the temperature at the bottom of the distillation-reactor ranges from about 500° F. to about 580° F.

15. The process of claim 10 wherein the temperature at the bottom of the distillation-reactor ranges from about 400° F. to about 700° F., and the total liquid residence time ranges from about 10 minutes to about 2 hours.

16. The process of claim 10 wherein the temperature at the bottom of the distillation-reactor ranges from about 500° F. to about 580° F. and the total liquid residence time ranges from about 20 minutes to about 30 minutes.

17. The process of claim 10 wherein condensed liquid olefins are returned to the top of the distillation-reactor column as reflux in liquid:distillate ratio ranging from about 0.1:1 to about 10:1.

18. The process of claim 10 wherein condensed liquid olefins are returned to the top of the distillation-reactor column as reflux in liquid:distillate ratio ranging from about 0.2:1 to about 2:1.

* * * * *